(12) United States Patent
Xu

(10) Patent No.: US 8,100,970 B2
(45) Date of Patent: *Jan. 24, 2012

(54) BIOLOGICAL SURGICAL PATCH AND METHOD OF MAKING

(75) Inventor: Guo-Feng Xu, Guangzhou (CN)

(73) Assignee: Grandhope Biotech Co., Ltd. (CN)

( * ) Notice: Subject to any disclaimer, the term of this patent is extended or adjusted under 35 U.S.C. 154(b) by 623 days.

This patent is subject to a terminal disclaimer.

(21) Appl. No.: 11/639,604

(22) Filed: Dec. 15, 2006

(65) Prior Publication Data

US 2007/0142847 A1    Jun. 21, 2007

(30) Foreign Application Priority Data

Dec. 20, 2005  (CN) .......................... 2005 1 0120796

(51) Int. Cl.
*A61F 2/02* (2006.01)
*A61K 35/34* (2006.01)

(52) U.S. Cl. ................... 623/13.17; 623/23.72; 424/569
(58) Field of Classification Search ............... 623/13.17, 623/23.72; 424/569
See application file for complete search history.

(56) References Cited

U.S. PATENT DOCUMENTS

| | | |
|---|---|---|
| 3,974,526 A | 8/1976 | Dardik et al. |
| 4,083,066 A | 4/1978 | Schmitz et al. |
| 4,319,363 A | 3/1982 | Ketharanathan |
| 4,481,009 A | 11/1984 | Nashef |
| 4,597,766 A | 7/1986 | Hilal et al. |
| 4,765,335 A | 8/1988 | Schmidt et al. |
| 4,793,344 A | 12/1988 | Cumming et al. |
| 5,067,962 A | 11/1991 | Campbell et al. |
| 5,078,744 A | 1/1992 | Chvapil |
| 5,080,670 A | 1/1992 | Imamura et al. |
| 5,217,492 A | 6/1993 | Guire et al. |
| 5,290,217 A | 3/1994 | Campos |
| 5,416,074 A | 5/1995 | Rabaud et al. |
| 5,447,536 A | 9/1995 | Girardot et al. |
| 5,549,666 A | 8/1996 | Hata et al. |
| 5,733,339 A | 3/1998 | Girardot et al. |
| 5,741,283 A | 4/1998 | Fahy |
| 5,758,420 A | 6/1998 | Schmidt et al. |
| 5,902,338 A | 5/1999 | Stone |
| 5,955,110 A | 9/1999 | Patel et al. |
| 5,976,192 A | 11/1999 | McIntyre et al. |
| 5,984,858 A | 11/1999 | Stone |
| 6,008,292 A | 12/1999 | Lee et al. |
| 6,090,995 A | 7/2000 | Reich et al. |
| 6,106,555 A | 8/2000 | Yang |
| 6,117,979 A | 9/2000 | Hendriks et al. |
| 6,177,514 B1 | 1/2001 | Pathak et al. |
| 6,241,981 B1 | 6/2001 | Cobb et al. |
| 6,251,117 B1 | 6/2001 | Kringel et al. |
| 6,458,889 B1 | 10/2002 | Trolisas et al. |
| 6,482,584 B1* | 11/2002 | Mills et al. ............... 435/1.1 |
| 6,572,650 B1 | 6/2003 | Abraham et al. |
| 7,053,051 B2 | 5/2006 | Hendriks et al. |
| 7,060,103 B2 | 6/2006 | Carr, Jr. et al. |
| 7,077,851 B2 | 7/2006 | Lutze et al. |
| 2002/0042473 A1 | 4/2002 | Trolisas et al. |
| 2002/0081564 A1 | 6/2002 | Levy et al. |
| 2002/0091445 A1 | 7/2002 | Sung et al. |
| 2002/0099448 A1 | 7/2002 | Hiles et al. |
| 2002/0103542 A1 | 8/2002 | Bilbo |
| 2002/0138152 A1 | 9/2002 | Francis et al. |
| 2003/0013989 A1 | 1/2003 | Obemiller et al. |
| 2004/0202625 A1 | 10/2004 | Daniloff et al. |
| 2005/0119736 A1 | 6/2005 | Zilla et al. |
| 2005/0136543 A1 | 6/2005 | Torres et al. |
| 2008/0195229 A1 | 8/2008 | Quijano et al. |

FOREIGN PATENT DOCUMENTS

| | | |
|---|---|---|
| CN | 1445003 | 5/1999 |
| CN | 1237889 | 12/1999 |
| CN | 1267201 | 9/2000 |
| CN | 1313741 | 9/2001 |
| CN | 1330528 | 1/2002 |
| CN | 1456363 | 11/2003 |
| CN | 1473551 | 2/2004 |
| CN | 1556715 | 12/2004 |
| CN | 1579342 | 2/2005 |
| WO | WO9417851 | 8/1994 |
| WO | WO0232327 | 4/2002 |

OTHER PUBLICATIONS

Laurencin et al. 1999. Advancements in tissue engineered bone substitutes. Curr. Opin. Orthop. 10:445-451.*
IPO—PCT/CN2006/003419.
IPR—PCT/CN2006/003442.
IPR—PCT/CN2006/003443.
IPR—PCT/CN2006/003444.

* cited by examiner

Primary Examiner — Taeyoon Kim
(74) Attorney, Agent, or Firm — Raymond Sun

(57) ABSTRACT

A biological surgical patch made by a method that includes the steps of providing a natural animal tissue that has a substrate, crosslinking and fixing the substrate, minimizing the antigens from the substrate, tanning the substrate, and incorporating an active layer in the substrate.

14 Claims, 1 Drawing Sheet

BIOLOGICAL SURGICAL PATCH AND METHOD OF MAKING

BACKGROUND OF THE INVENTION

1. Field of the Invention

The present invention relates to a medical prosthesis for human implantation, and in particular, to a surgical patch that is used for repairing tissues or organs during surgery.

2. Description of the Prior Art

Repair of defective tissues and organs is often required in modern surgical techniques, for example, repair of dura mater, repair of defective pleura, repair of peritoneum, repair of hernial strain, repair of diaphragm, repair of blood vessels, repair of atrial septum, repair of pericardium, repair of kidneys, etc. There are many "surgical sticking patches" that are currently being provided to meet clinical demands. However, these products were first prepared with synthetic materials.

These synthetic materials utilized in preparing the surgical sticking patches include polypropylene, polyethylene, polyamide, Dacron resin, polytetrafluoroethylene, silicone gel, and carbon fiber, among others, which are foreign to the human body and that remain permanently in the repaired tissues. These materials often lead to non-bacterial inflammatory diseases due to physical irritation and complications caused by chronic rejective reaction.

Other patches have been prepared with absorbable synthetic materials such as polyglycolic acid (PGA), polylactic acid (PLA) and copolymer thereof (PGA-PLA). However, the rate of degradation of these materials is difficult to control to coincide with the rate of tissue recovery, so the efficacy is often uncertain due to rapid degradation. In addition, the degraded products can bring local acidity which affects normal healing of the repaired tissues.

Animal membrane tissues such as fascia and bovine pericardium have also been utilized in recent years through conventional processes including defatting, cell removal and fixation with glutaraldehyde, but elimination of antigens is hardly effective because cell removal is employed as the only means for eliminating antigens. Additionally, fixation of tissues with glutaraldehyde is achieved by crosslinking through acetalization, and glutaraldehyde is released during degradation, leaving residual toxicity and causing more potent cellular toxicity so that its growth in the inherent tissue becomes difficult, resulting in poor repair effect.

SUMMARY OF THE DISCLOSURE

It is an object of the present invention to provide a biological surgical patch having no immune rejection with good biocompatibility and safe/reliable application, and a method of preparation thereof.

In order to accomplish the objects of the present invention, the present invention provides a biological surgical patch made by a method that includes the steps of providing a natural animal tissue that has a substrate, crosslinking and fixing the substrate, minimizing the antigens from the substrate, tanning the substrate, and incorporating an active layer in the substrate.

DETAILED DESCRIPTION OF THE PREFERRED EMBODIMENTS

Figure 1:
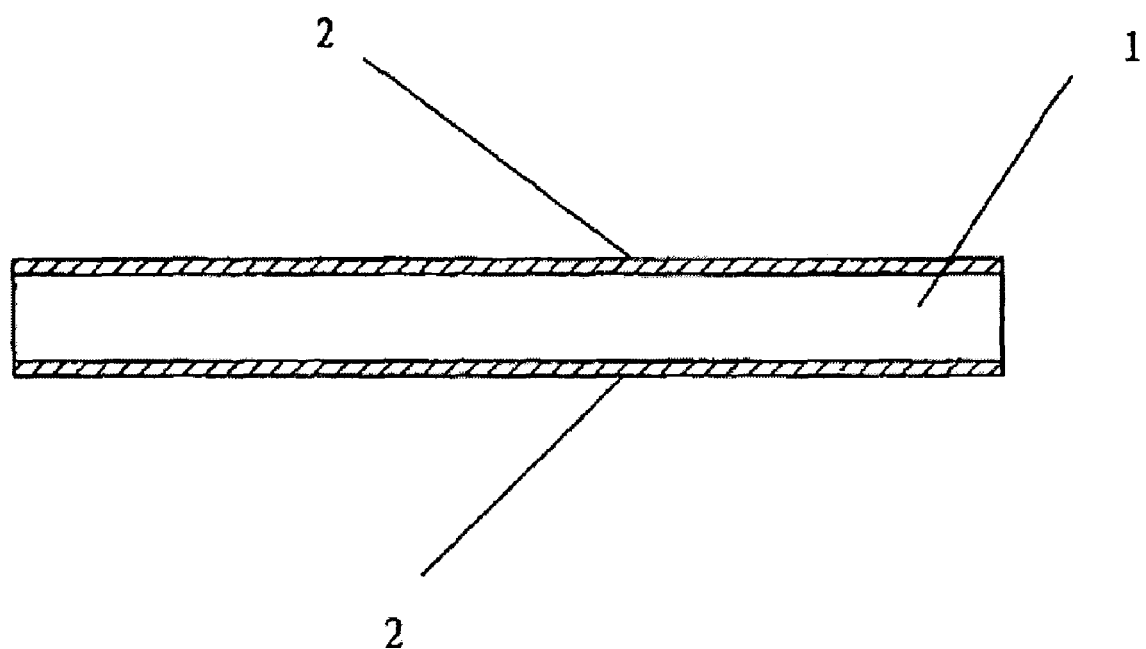
FIG. 1 is a cross-sectional view of a surgical patch according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a biological surgical patch comprising a substrate prepared from animal membrane tissues, treated with crosslinked fixation with a non-aldehyde fixative, and then treated to minimize antigens.

Animal membrane tissues are easily degraded or decomposed by microorganisms, so that crosslinking and fixation with a fixative is required. Conventionally, glutaraldehyde is utilized as a fixative, but glutaraldehyde produces toxic radicals. Aldehydes undergo crosslinking with proteins through the acetal reaction and toxic aldehydes are released when the crosslinked products are degraded, so that products fixed with an aldehyde have long-term residual toxicity. When non-aldehyde fixatives such as epoxides, diacyl diamides, diisocyanates, polyethylene glycol or carbodiimides are utilized as fixatives in place of aldehydes, this toxicity problem can be minimized or even eliminated. For example, when an epoxide is utilized to replace aldehyde-type fixatives, a ring-opening/crosslinking reaction occurs readily because epoxides are unstable, but the crosslinking product can be made very stable and not easily degraded by controlling the reaction condition. It is slowly degraded into polypeptides and amino acids and absorbed only when tissue growth and regeneration begin to devour it by secreting kallikrein, fibrinolysin and glucocorticoid hormone to help collagenase in the degradation. Such kind of passive degradation and tissue regeneration are occurring synchronously which is beneficial to tissue regenerative repair while having no residual toxicity of aldehydes. According to modern immunological theory, the antigenicity of animal tissues stems mainly from active groups located at specific sites and in specific conformations, and these active groups include —OH, —NH2, —SH, etc. The specific conformations result mainly from some specific hydrogen bonding formed by spiral protein chains. The specific sites and conformations are called antigen determinants. One or more active reagents (e.g., acid anhydrides, acyl chlorides, amides, epoxides, etc.) that react readily with these groups are utilized to bond with and block these groups when treating animal tissues so that the antigens can be effectively minimized or eliminated. Simultaneously, reagents with strong hydrogen bonding (e.g., guanidine compounds) are utilized to replace the hydrogen bonding that gives the specific configurations so that the configurations are altered and the antigenicity is effectively eliminated.

Tanning

The present invention uses an additional cross-linking method and a protein grafting method as a tanning process to improve the mechanical strength and toughness of the tissue. In this regard, a piece of animal membrane tissue usually provides poor mechanical properties (after harvesting). As used herein, "mechanical properties" means strength, toughness, rigidity and modulus. Both cross-linking and protein grafting can alter the mechanical properties of the tissue collagen (protein) matrix. Although cross-linking and protein grafting are common methods that are used to improve the mechanical properties of high polymers, it is still important to carefully determine the selection of reagents as well as the reaction conditions because protein can often be denatured. The length, density and distribution of cross-linkage are properly designed to ensure the stability of the tissue material and mechanical property.

For example, the molecular chain length of the crosslinking agent determines the cross-linking length. A longer chain results in better material flexibility. However, larger molecular chains are more difficult to penetrate into the collagen matrix. For example, when selecting an epoxy compound as the cross-linking agent, the molecular chain is preferably 4-8 hydrocarbons. The cross-linking density determines the cross-linking degree. Denser cross-linking results in better material stability, but denser cross-linking (especially when combined with a shorter molecular chain) can introduce a higher local stress in the material. A relatively uniform distribution of the cross-linking is ideal, but is usually difficult to obtain. Utilizing a lower concentration of the cross-linking solution, under a lower temperature, longer reaction duration, and repeating a few more times with the same reaction can often yield better results. As an example, when using an epoxy compound as the cross-linking agent as described in U.S. Pat. No. 6,106,555, good material stability, good flexibility, toughness and strength can be obtained by picking 4-8 hydrocarbon atom chain, with a concentration of 0.1 to 2%, under 4 to 24 degrees Celcius, reaction for 3-10 days, and repeating 2 to 5 times.

The chemical reagents can be the same as those described herein for use with tissue fixation. The protein grafting process can further improve the tissue's mechanical strength, toughness, rigidity and modulus. Protein grafting requires a large amount of polymer chains so that the nature of the protein structure can be changed substantially. Some high polymers can be grafted into collagen molecules by means of polycondensative primers. In order to avoid introducing hazardous subject matter into the human body, it is preferable to use biodegradable high polymers as the grafting agents, such as polyglycolic acid (PGA), polylactic acid (PLA) and others. These biodegradable polymers can be metabolized in the host environment through a tracarboxylic acid cycle just like for carbohydrates or fat metabolism. After such an extensive protein modification, up to 25 kGy gamma ray sterilization can be applied without adversely affecting the mechanical property of the tissue material. The total amount of protein grafting can be controlled optimally.

Method

A method of preparing the biological surgical patches according to the present invention comprises the following steps, and uses animal membrane tissue as the substrate:

1. Selection of materials and pretreatment: Fresh animal membrane tissues are collected and trimmed to remove excessive impurities and irregular parts. Examples of animal membrane tissues that can be used include animal diaphragm, pleura, pericardium, omentum or intestinal membrane.

2. Alkaline treatment: The membrane tissues are soaked in an alkaline solution. The alkaline solution can be NaOH, KOH or Ca(OH)$_2$ solution.

3. Defatting: Fats and fat-soluble impurities in the substrate are extracted with an organic solvent.

4. Crosslinking fixation: The collagen molecules in the substrate are crosslinked and fixed with a non-aldehyde fixative, as described in greater detail hereinbelow.

5. Minimizing antigens: An active reagent is utilized to block the specific active groups such as —OH, —NH2, —SH, etc., in the proteins of the substrate, and a reagent with strong hydrogen bonding power is utilized to replace the specific hydrogen bonding in the spiral chains of the protein molecules in the substrate and alter its specific configuration.

6. Tanning process: First, the preformed polymers are produced from monomers by synthesis. Second, the substrate is dehydrated with alcohol. Third, the preformed polymers are then grafted into collagen molecules by means of polycondensative primers. When using PGA as the grafting reagent, a small amount of glycolide may be used as the polycondensative primer. When using PLA as the grafting reagent, a small amount of lactide may be used as the polycondensative primer.

For example, using PLA as the protein grafting agent, the process could take 30-50 mg of lactide and dissolve it in 1000 ml of chloroform. 2-3 grams of triisobutyl aluminum can be added as the composite catalyst, and this solution can be stir-mixed for one to two hours under a temperature of 40-60 degrees Celcius. 100 ml of a 0.1 N NaOH solution is then added and stir-mixed for 30-60 minutes to destroy the catalyst. Then take away the separated water layer (with catalyst) and have the preformed polymers ready. Immerse the dehydrated substrate into the preformed polymer solution. Add 0.1 to 2 g of lactide and 0.5 to 5 g of proprionic anhydride as an initiation catalyst and then stir-mix for 24 hours under a temperature of 34 to 40 degrees Celcius. Take out the substrate and put it into chloroform to clean away the residual preformed polymers. After rinsing with saline, the substrate is then immersed into saline for 12 to 24 hours to recover the water content. The substrate is now ready for the next processing step.

7. Surface modification with active layer to induce activity: A process of modifying and activating the surface of the substrate, by coupling the substrate surface with active substances such as polypeptides or glycosaminoglycans which are capable of adhering to growth factors, to form an active surface layer, using a coupling agent. The coupling agent can be a diacyl diamide, diacid anhydride, diepoxide or other bifunctional reagents capable of carrying out condensation with —NH$_2$, —OH and —COOH.

Fixative

The fixative applied in step 4 of the above method can be a reagent that crosslinks easily with protein molecules and is one or two reagents selected from epoxides, diacyl diamides, diisocyanates, polyethylene glycol or carbodiimides. This fixative may be an epoxy compound that has a hydrocarbon backbone, that is water-soluble, and which does not contain an ether or ester linkage in its backbone. This fixative is described in U.S. Pat. No. 6,106,555, whose entire disclosure is incorporated by this reference as though set forth fully herein. Examples include an epoxide, a diamide, a diisocyanate, a polyethylene glycol, or a carbodiimide, in that the epoxide may be a monocyclic epoxide, or a bicyclic epoxide, or it may be a low poly(epoxide) (such as low poly(ethylene oxide), poly(propylene oxide) or a glycidyl ether). The epoxide may be a monocyclic epoxide

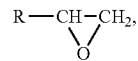

or a dicyclic epoxide

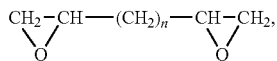

where R=H, $C_nH_{2n+1}$—, n=0-10, and may also be a lower polyepoxide such as polypropylene oxide.

Active Reagents

The active reagents in step 5 of the above method may be low molecular weight organic acid anhydrides, acyl chlorides, acyl amides or epoxides, and the reagents having strong hydrogen bonding power are guanidine compounds.

Modification for Strength Improvement

In step 6 above, the substrate is modified by strengthening it with proteins to prepare a strong substrate. Because some membrane tissues lack the required mechanical strength for practical application, such as hernia repairing patches, and the mechanical strength is often reduced during biochemical treatment, appropriate grafting is conducted on collagen molecules, in that polyamide, polyamine, polyester polylactic acid or polyglycolic acid fragments are suitably grafted on the collagen molecules. The materials utilized are the prepolymers of these materials and the methods include polymer grafting methods such as condensation, induction and irradiation. This modification improves the mechanical strength and toughness of the substrate.

Active Layer

The active layer in step 7 above is incorporated on the surface by coupling it with an active component such as a polypeptide or glycosaminoglycan. One example of the polypeptides is the polypeptide obtained from the condensation of 16 lysines (K16), glycine (G), arginine (R), asparagic acid (D), serine (S), proline (P) and cysteine (C), and the glycosaminoglycan is hyaluronic acid, chondroitin sulfate, dermatan sulfate, heparin, acetylheparin sulfate or keratan sulfate. These polypeptides or glycosaminoglycans exhibit a broad-spectrum adherence and enriching effect for growth factors or activate undifferentiated cells to perform oriented differentiation so that they are capable of exercising the function of inducing regenerative repair of organic tissues.

The present invention provides the following advantages. The original materials are animal membrane tissues comprising collagen as the main component which can be degraded at a rate that coincides with the growth rate of tissue regeneration, and the products of degradation are 20 different amino acids or polypeptides that can be absorbed by the body, which are beneficial to the regenerative repair of the defective tissues. The surgical patches of the present invention exhibit no immune rejection and have good biocompatibility and can induce and promote tissue regeneration while having mechanical property that meets the mechanical requirements of the tissues for repair.

EXAMPLE 1

As shown in FIG. 1, the biological surgical patch comprises (i) a substrate 1 prepared from porcine or bovine pericardium by crosslinking fixation with a non-aldehyde fixative, eliminating antigens and improving the strength with a protein, and (ii) active surface layers 2 formed by on both the top and bottom surfaces of substrate 1 by coupling an active component such as a specific polypeptide or glycosaminoglycan. One example of the polypeptides is the polypeptide obtained from the condensation of 16 lysines (K16), glycine (G), arginine (R), asparagic acid (D), serine (S), proline (P) and cysteine (C), and the glycosaminoglycan is hyaluronic acid, chondroitin sulfate, dermatan sulfate, heparin, acetylheparin sulfate or keratan sulfate.

The method of preparation of the biological surgical patch of the present invention includes the following steps, using porcine or bovine pericardium as the substrate:

1. Selection of materials and pretreatment: Fresh porcine or bovine pericardium are collected from slaughterhouses managed by professionals in accordance with regulations while contact with pollutants is avoided. Preliminary sterilization is performed using a broad-spectrum antibacterial agent such as benzalkonium chloride, sodium azide and chlorhexidine and the impurities and irregular portions are removed and trimmed.

2. Alkaline treatment: Soaking of the substrate 1 in NaOH, KOH or $Ca(OH)_2$ solution is conducted for several hours.

3. Defatting: Fats and fat-soluble impurities in the substrate 1 are extracted with an organic solvent such as chloroform, ethyl acetate, anhydrous alcohol or mixtures thereof.

4. Crosslinking fixation: The collagen molecules in the substrate 1 are crosslinked and fixed using epoxide or polyethylene glycol solution as a fixative.

5. Elimination of antigens: The specific active group, namely —OH or —$NH_2$ or SH, in the proteins of the substrate 1 is blocked with an active reagent such as a small-molecule organic acid anhydride, acyl chloride, acyl amine and monocyclic oxide, and the specific hydrogen bonding in the spiral chains of the proteins in the substrate 1 is replaced by using a reagent such as a guanidine compound with strong hydrogen bonding.

6. Tanning process: Utilizing PLA as the grafting reagent, a small amount of lactide is used as the polycondensative primer.

7. Surface modification to induce activity: An active component such as a specific polypeptide or glycosaminoglycan is coupled onto the surface of substrate 1 by using a coupling agent such as diacyldiamine or diacid anhydride or epoxide or other bifunctional reagents capable of carrying out condensation with —$NH_2$, —OH and —COOH groups to form the active surface layers 2 on the two surfaces of substrate 1.

8. Packaging: Washing, packing and sealing while sterilizing by irradiating with Cobalt-60.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A biological surgical patch comprising a natural animal tissue that has a substrate comprising collagen molecules, the substrate having: (i) been fixed with crosslinking reagents, (ii) specific active groups in protein molecules of the substrate that have been blocked by at least one active reagent after fixation by the crosslinking reagents, (iii) specific conformation of protein molecules of the substrate altered by a reagent with a guanidine compound, (iv) preformed polymers have been grafted into the collagen molecules by polycondensative primers wherein the polymers are polyglycolic acid (PGA) with glycolide as the polycondensative primers or the polymers are polylactic acid (PLA) with lactide as the polycondensative primers, and (v) an active layer coupled to the surface of the substrate, the active layer including either a polypeptide or a glucosaminoglycan that has the ability to adhere growth factors after implantation.

2. The patch of claim 1, wherein the substrate is fixed by an epoxide, a diamide, a diisocyanate, or a carbodiimide.

3. The patch of claim 1, wherein the at least one active reagent to block specific active groups in the protein molecules of the substrate is selected from the group consisting of acid anhydrides, acryl chlorides, and acylamides.

4. The patch of claim 2, wherein the epoxide has a hydrocarbon backbone, that is water-soluble, and which does not contain an ether or ester linkage in its backbone.

5. The patch of claim 1, wherein the natural animal tissue is pericardium.

6. A surgical patch for implantation into a human body, the patch made by a method comprising:
isolating from a host a natural animal tissue that has a substrate comprising collagen molecules;

crosslinking and fixing the substrate with a cross-linking reagent;

blocking residual specific active groups in protein molecules of the substrate after fixation by applying at least one active reagent;

altering the specific conformation of protein molecules of the substrate by a reagent with a guanidine compound;

grafting preformed polymers into the collagen molecules by polycondensative primers, wherein the polymers are PGA with glycolide as the polycondensative primers or the polymers are PLA with lactide as the polycondensative primers; and coupling an active layer to the surface of the substrate that includes either a polypeptide or a glucosaminoglycan that has the ability to adhere growth factors after implantation.

7. The patch of claim 6, wherein the substrate is fixed by an epoxide, adiamide, a diisocyanate, or a carbodiimide.

8. The patch of claim 6, wherein the at least one active reagent to block specific active groups in the protein molecules of the substrate is selected from the group consisting of acid anhydrides, acryl chlorides, and acylamides.

9. The patch of claim 7, wherein the epoxide has a hydrocarbon backbone, that is water-soluble, and which does not contain an ether or ester linkage in its backbone.

10. The patch of claim 7, wherein the natural animal tissue is pericardium.

11. The patch of claim 1, wherein the at least one active reagent is different from the crosslinking reagent.

12. The patch of claim 3, wherein the substrate is fixed by an epoxide, a diamide, a diisocyanate, or a carbodiimide.

13. The patch of claim 6, wherein the at least one active reagent is different from the crosslinking reagent.

14. The patch of claim 8, wherein the substrate is fixed by an epoxide, a diamide, a diisocyanate, or a carbodiimide.

\* \* \* \* \*